United States Patent [19]

Cinotti et al.

[11] 4,245,988
[45] Jan. 20, 1981

[54] APPARATUS AND METHOD FOR FITTING FALSE TEETH

[76] Inventors: William Cinotti, 3285 Kennedy Blvd., Jersey City, N.J. 07028; Harold Gelb, 435 E. 57th St., New York, N.Y. 10022; Arthur Grieder, 203 Godwin Ave., Ridgewood, N.J. 07450

[21] Appl. No.: 969,940

[22] Filed: Dec. 15, 1978

[51] Int. Cl.³ ............................................. A61C 19/04
[52] U.S. Cl. ..................................... 433/68; 433/213
[58] Field of Search ............... 32/2; 433/213, 37, 171, 433/68

[56] References Cited

U.S. PATENT DOCUMENTS

| | | | |
|---|---|---|---|
| 2,685,133 | 8/1954 | Greene et al. | 32/2 |
| 3,335,495 | 8/1967 | Wichner | 32/2 |
| 3,460,252 | 8/1969 | Schneider | 32/2 |
| 3,465,440 | 9/1969 | Galeis | 32/2 |
| 3,644,996 | 2/1972 | Weinkle | 32/2 |
| 3,909,944 | 10/1975 | Schmidt et al. | 32/2 |
| 3,987,546 | 10/1976 | Trampe | 433/213 |
| 4,097,992 | 7/1978 | Hazar | 32/2 |
| 4,133,110 | 1/1979 | Bernstein et al. | 433/213 |

*Primary Examiner*—Robert Peshock
*Attorney, Agent, or Firm*—Pennie & Edmonds

[57] ABSTRACT

An apparatus and a method for making denture models used in fabricating dentures customized for a given patient. The apparatus of the present invention is a moldable impression member which conforms to a portion of the mouth and comprises an alterable block member disposed on the nonimpression surface of the impression member. The block member is representative of teeth and generally corresponds to the dimensions and positioning of such teeth. The present invention includes a method directed to selecting an impression member and adjusting it to the patient. The block member particularly is adjusted to provide a customized fit. The impression members are preferably made of wax.

47 Claims, 3 Drawing Figures

APPARATUS AND METHOD FOR FITTING FALSE TEETH

TECHNICAL FIELD

The invention relates to prosthodontics and more particularly to a method and article for forming, adjusting and fitting denture models useful for fabricating customized dentures.

BACKGROUND ART

The making and fitting of dentures is old in the art. However, the making and fitting of dentures in the past has been a time-consuming process requiring the skill of a dentist as well as a technician skilled in fabricating the final denture forms. As a result, the cost of dentures as well as the inconvenience resulting from the time required between measurement and final fitting has dissuaded many people, especially the indigent, from obtaining dentures.

Usually a dentist would make an impression of the patient's gums and the palate if an upper denture is required. A dental technician receives the impression and makes a plaster cast which he places in an articulator which simulates movement of the patient's jaws. After pouring a wax base plate on the cast, false teeth are positioned in the wax. The wax denture is then tried on the patient by the dentist who makes corrections thereto and returns the same to the technician. The technician is only then able to prepare the finished denture product which still requires additional time and tools.

Known methods and apparatus for making and fitting dentures are both disclosed and illustrated in U.S. Pat. Nos. 2,685,133 to Greene et al.; 3,335,495 to Wichner; 3,460,252 to Schneider; 3,644,996 to Weinkle; and 3,909,944 to Schmidt et al.

The Greene patent discloses a method of fitting dentures which comprises selecting from a plurality of different presized upper and lower ridge forms until correctly fitting forms are found. Specifically three standard ridge forms are used. Next prefabricated dentures having tooth facings and corresponding to the selected ridge forms are lined with an impressionable thermosetting bonding material. The prefabricated dentures are then aligned with the gums and are positioned in occlusion into conforming engagement with the gums. After a sufficient time the thermosetting material hardens and provides denture fits for the gums.

The Wichner patent discloses a method of making and fitting dentures by employing a denture base which utilizes an intermediate blank attached to the base and having posts projecting therefrom to receive a plurality of separate individual artificial teeth which are finally adhered to the posts.

The Schneider patent discloses a method and an article for forming a denture which includes a flexible U-shaped tray which has depressions therein for placement of false teeth. A moldable resin which is poured into said tray can be shaped by inserting the tray into the user's mouth and applying pressure to the resin through a protective means such as a polyvinylide chloride film.

The Weinkle patent discloses a prefabricated denture construction and method which involves selection of a suitable ridge form from as many as ten different sizes to which there corresponds a denture base. The denture base is lined on its inner surface with a moldable lining material which tailors the denture base to the jaw of the patient. Artificial teeth can then be attached individually or in groups to complete the denture. If necessary, a further finishing step may include removal of excess lining material which would squeeze out over the ridges of the denture.

The Schmidt patent discloses a denture and method of making the same. A unitary wax pattern of appropriate size is selected. The wax pattern has an arc-shaped channel similar to the denture and simulating the gingival tissue. The wax pattern on its outer base structure has a plurality of sockets adapted for receipt of artificial teeth. Fitting of the wax pattern to a ridge of the mouth is accomplished by using impressionable material. In the final stage artificial teeth are chosen and inserted into sockets which are provided in the base structure of the wax pattern. After additional functional checks of the bite, the wax pattern is converted to a final denture base material by means of conventional processing procedures.

Although each of the above-mentioned patented methods and products produced thereby is useful in varying degrees, they all suffer from disadvantages to some degree.

The above patents do not provide for a complete customizing of the dentures to the mouth of a patient. After the placement of teeth on the denture form or pattern, further adjustment of the form to account for proper labial aspect, centric occlusal relation, or interocclusal space is difficult to accomplish. Moreover, the Greene and Weinkle patents with their predetermined ridge forms and corresponding prefabricated dentures and the Wichner patent with its intermediate blanks provide undue multiplicity of parts.

DISCLOSURE OF INVENTION

The method and apparatus of the present invention for making dentures are a significant improvement over the devices and methods discussed above and overcome the limitations found therein. The method and apparatus of the present invention provides a denture form or model which exhibits a higher degree of customized precision not previously available with the prior art. Not only does the method and apparatus disclosed and claimed herein permit a quicker turnaround for completing a denture during a single visit to the dentist, but also greatly reduces the cost thereof.

The method of the present invention is directed to making denture models for use in fabricating dentures customized for a given patient. The method comprises first the step of selecting a maxillary and mandibular moldable impression member which are adapted to conform respectively to the upper and lower portions of the mouth of the patient and to receive an impression of the respective portions. The impression members each comprise an alterable block member disposed on the non-impression surface of the impression member. The block member is representative of teeth and generally corresponds to the dimensions and positioning of such teeth. A first set of measurements of the mouth of the patient are taken and transferred to the impression members. Then a first adjustment of the impression member is made. Next the impression members are placed in contact with their respective portions of the mouth of the patient and are molded to receive the impressions and shape of the respective mouth portions. A second adjustment of the impression member is then made. The impression surfaces of the impression members are coated with an impressionable material and are placed in contact with their respective portions of the mouth of the patient such that the impressionable material receives and retains the respective impressions thereof. Next a third adjustment of the impression members is made. Casts of the impression surfaces of the impression members are made and mounted with the impression members attached thereto in an articulator. The block members are removed and the corresponding teeth are set in place thereof. A final fitting of impression members in the patient's mouth is made. Finally, a post palatal seal is established for the maxillary impression member.

The method of the present invention is also directed to making either a maxillary or mandibular denture form alone.

The present invention also relates to apparatus used for making the customized denture forms. An apparatus of the present invention is a moldable impression member adapted to conform to a portion of the mouth of the patient and to receive an impression of said portion. The impression member comprises an alterable block member representative of teeth and generally corresponding to the dimensions and positioning of such teeth. The apparatus upon being placed in the mouth of a patient can thus be suitably formed and fitted thereto and thereby customized to provide a denture model.

An apparatus of the present invention for making upper denture models is a moldable impression member adapted to conform to an upper portion of the mouth of said patient and to receive an impression of said upper portion. The impression member comprises an inner wall and an outer wall attached to the inner wall so as to define a channel disposed between the walls and adapted to receive and contact the alveolar ridge of the upper mouth. A base is contiguous with the edges of the inner wall and is adapted for contacting the palate of the upper mouth and retaining the impression thereof. The impression member also comprises an alterable block member disposed on the non-impression surface of the impression member extending substantially along the length thereof. The block member is representative of teeth and generally corresponds to the dimensions and positioning of such teeth. The apparatus upon being placed in the upper portion of the mouth of a patient can thus be suitably formed and fitted thereto and thereby customized to provide an upper denture model.

An apparatus of the present invention for making lower denture models comprises the same elements of the apparatus for making upper denture models except that no base is needed for the lower denture model.

The impression members of the present invention can be made of any suitable moldable material and are preferably made of a wax, such as pink baseplate wax, suitable for making dental models. In a preferred embodiment, the block member is modified to provide a vacant area in the bicuspid-molar region.

BEST MODE FOR CARRYING OUT THE INVENTION

Figure 1:
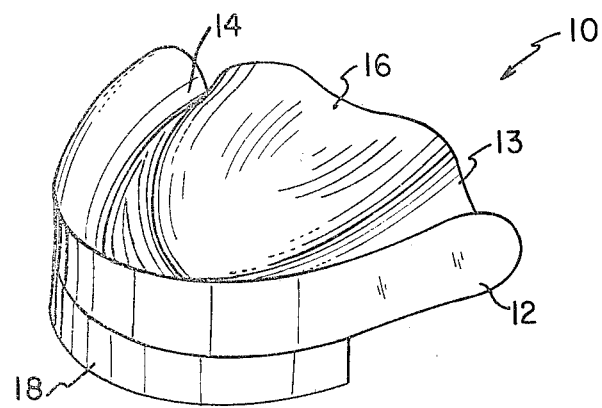
FIG. 1 is a perspective view of a maxillary impression member according to the present invention.

Referring to FIG. 1, a maxillary moldable impression member or rim tray 10 according to the present invention is shown for the upper denture. The maxillary tray 10 has a base portion 16 which seats against the palate of the upper mouth. The maxillary tray 10 has an outer side wall 12 and an inner wall 13 which curves toward the base portion 16 thereby forming an arched channel 14 which is adapted to generally contact the upper alveolar ridge, i.e., a ridge of bone to which teeth are attached. A block member 18 is positioned on maxillary tray 10 in correspondence to the positioning of artificial teeth thereon. However the bicuspid-molar region is preferably left vacant. The purpose of this vacant region will be explained herein.

Figure 2:
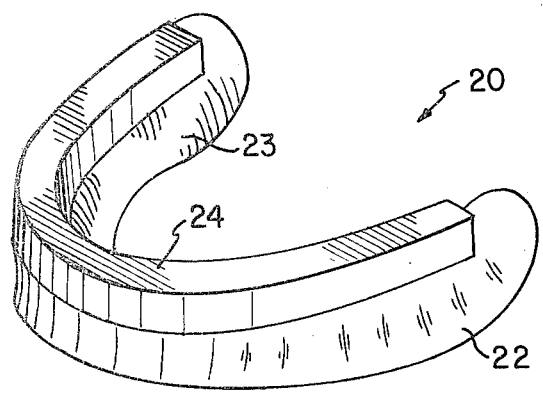
FIG. 2 is a perspective view of mandibular impression member according to the present invention.

Turning now to FIG. 2, a mandibular moldable impression member or rim tray 20 according to the present invention is illustrated for the lower denture. The mandibular tray 20 includes an outer side wall 22 and an inner wall 23 which form an arched channel (not shown) adapted to generally contact the lower alveolar ridge. A block member 24 is positioned on the mandibular tray 20 in correspondence to the positioning of artificial teeth thereon.

Both trays 10, 20 are preferably made of a dental wax such as paraffin, beeswax, or carnauba wax. However, any suitable moldable material may be used. This composition allows the trays 10, 20 to be formed to a desired shape and to be marked where necessary. As U.S. Pat. No. 2,685,133 to Greene et al. discloses, it has been ascertained that 98% of most people requiring dentures have jaw contours falling within one of three different standard sizes. Thus a dentist stocking only three different sizes for both the maxillary 10 and mandibular trays 20 can be assured of having a suitable size for any patient.

Figure 3:
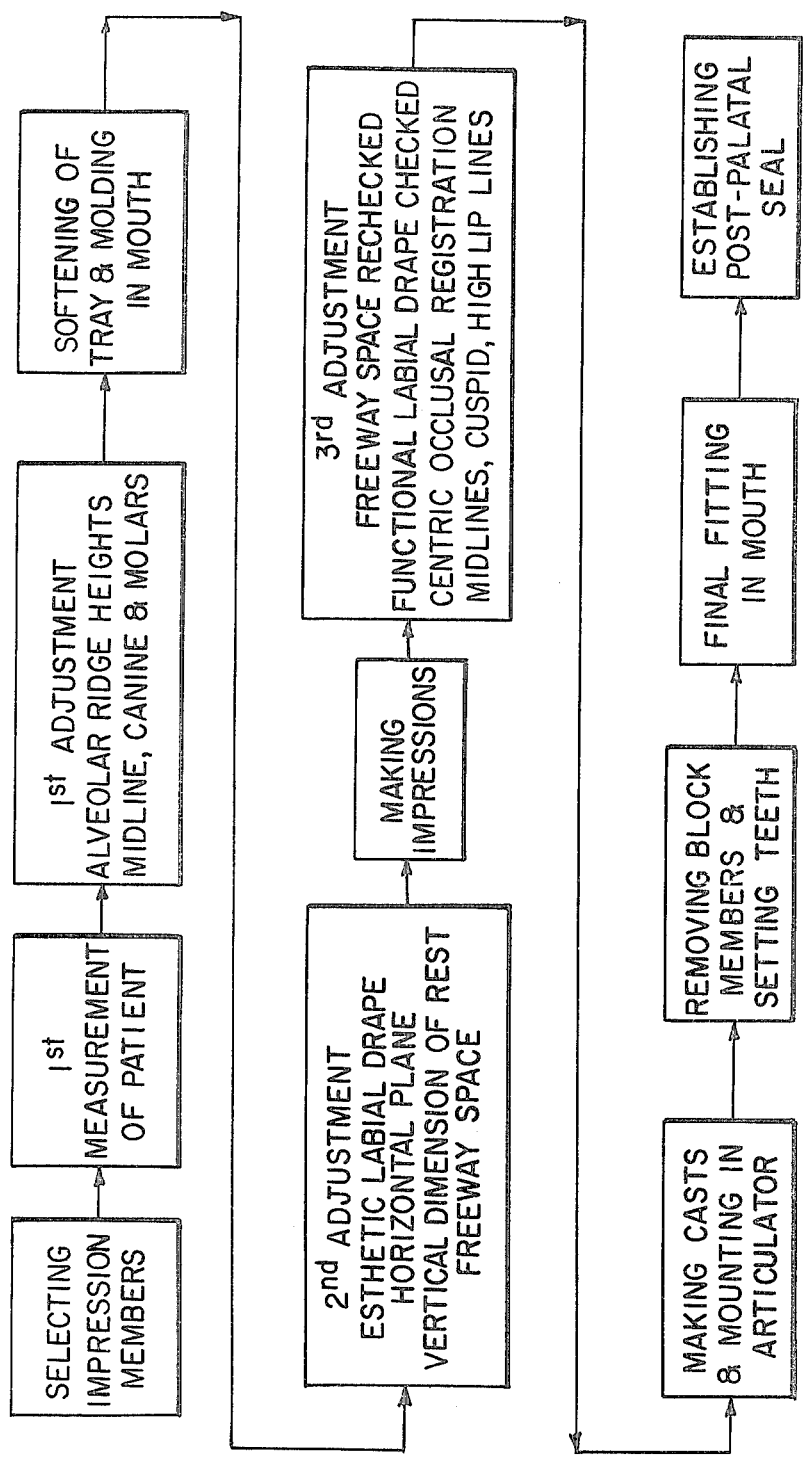
FIG. 3 is a block diagram diagrammatically illustrating the method of the present invention.

The method of making, fitting, and adjusting dentures according to the present invention is diagrammatically illustrated in FIG. 3.

A dentist initially chooses a suitably sized maxillary 10 and mandibular 20 moldable impression member or rim tray. A first set of measurements of the patient and a first adjustment of the trays 10, 20 are made. By means of a periodontal probe or measuring device, the depth of the mucobuccal fold is measured. The measuring device is placed vertically on the facial aspect of the alveolar ridge, a ridge of bone to which teeth are attached in the maxilla and mandible, respectively the bones of the upper and lower jaws. Thereby the distance from the crest of the alveolar ridge to the mucobuccal fold is measured. By using the same measuring device, the above-mentioned distance is transferred to the inside of the trays 10, 20 and marked thereon. Also recorded and marked on the trays 10, 20 are the midline, canine, and second molar positions. The markings made are joined together by use of a knife or spatula. Then the knife or spatula is heated and used to cut away the peripheral wax area above the line created. The trays 10, 20 when placed in the mouth therefore do not impinge on the mucobuccal fold.

The trays 10, 20 are then softened by placing the trays 10, 20 in a hot water bath maintained at approximately 120° F. for approximately one minute or until the wax composition of the trays 10, 20 has softened without melting. The trays 10, 20 are then placed in the mouth and molded to the tissues therein by pressing on the trays 10, 20 with the fingers of one hand while holding the respective trays 10, 20 with the other hand. Before the wax is hardened, the patient is instructed to pucker his lips and draw in a breath thereby assuring the molding of the peripheral area of the trays 10, 20, i.e., the portions of the trays 10, 20 adjacent the base of the alveolar ridge. It is necessary to assure that the tubersites as well as the retromolar pads and the retromylohid areas are completely covered. In the case of the maxillary rim impression tray 10, the base portion 16 must also be pressed and molded to conform to the palate or the roof of the mouth. The palate consists of a hard portion, the anterior two-thirds of the roof of the mouth, and a soft portion, the posterior one-third. The maxillary tray 10 is dimensioned such that a portion thereof contacts part of the soft palate as will be described herein.

A second adjustment of the trays 10, 20 is then performed. The labial or lip aspect of the maxillary tray 10 is reduced until the upper lip assumes an esthetic appearance.

The horizontal plane of the maxillary tray 10 can then be developed. First the length from the base of the nose to the end of the lip is measured without the trays 10, 20 in the mouth thereby permitting determination of whether the patient has a long, short, or average length. The applicants have found generally that an average length is approximately 24-25 mm, a short length approximately 21-23 mm, and a long length approximately 26-28 mm. The maxillary tray 10 is placed in the mouth and the same length measured. For average length lip patients, the lower aspect or edge of the block member 18 should show approximately 1 to 2 millimeters (mm) below the upper lip when the lips are slightly parted. For long length patients, none of the block member 18 should show, while for short length patients, approximately 2 or more mm should show. The maxillary tray 10 is adjusted in accordance with the above requirements and the lower aspect of the maxillary tray 10 is made parallel to a ruler held parallel to the interpapillary line. In this fashion the horizontal plane or low lip line is established.

Next the vertical dimension of rest can be developed. With the maxillary tray 10 in the mouth, the patient is asked to swallow and repeat the letter "m", and to allow the lips to touch gently without any pressure. The head should be in an unsupported position. The distance between a mark on the nose and on the chin is measured in mm three times and the average recorded. The lips are to be slightly touching when this is done. The mandibular tray 20 is placed in the mouth and the patient is told to close until the trays just contact each other. The mandibular tray 20 is reduced until it is flush with the maxillary tray 10 both vertically and horizontally. With the trays 10, 20 contacting and with the lips touching, the distance between the nose and chin is measured and compared against the measurement obtained earlier. It should be approximately 3 mm less than the earlier measurement obtained. If it is less than 3 mm, then the mandibular block 18 can be appropriately reduced or cut away. This establishes 3 mm of interocclusal or freeway space.

Adequate freeway or interocclusal space is next checked. With both trays 10, 20 in the mouth, the patient is instructed to count from 1 to 10, repeating the number six a few times while counting in sequence. The lips will spread when the patient speaks the number six and the wax trays 10, 20 will be seen. Approximately 1 mm of space between the wax trays 10, 20 should exist when the patient repeats the number six. If not, the mandibular tray 20 should be reduced 1 mm at a time until the 1 mm freeway space is observed between the blocks when the patient repeats the number six.

Alternatively, the 3 mm interocclusal or freeway space can be obtained by first providing a mandibular block member height such that the retromolar pad is bisected by the mandibular tray's level plane. Then the step developing the vertical dimension of rest described above is followed. In this manner a 3 mm interocclusal or freeway space is established without having to reduce the mandibular tray 20 a mm at a time as described above.

Impressions are then made in the channels 14 of both trays 10, 20. The inside of the maxillary tray 10 is coated with a rubber base adhesive. Equal amounts of a base and a catalyst elastic impression material are mixed for a minute. The material is placed in the maxillary tray 10 in the mouth, the patient is told to pucker the lips and to move the cheeks as if chewing. After six minutes the tray 10 is removed. Similarly, the adhesive is applied to the mandibular tray 20 and the impression material is placed in the tray 20. The tray 20 is placed in the mouth. Holding the tray 20 in position, the patient brings his tongue forward to the maxillary lip and then side-to-side. After six minutes remove the tray and check.

The impressions are replaced in the mouth and the patient is told to count from one to ten with a repetition of the number six. There should be 1 mm freeway space when the patient speaks the number six. If not, enough wax from the tray 10, 20 is removed until the space is established.

A third adjustment of the trays 10, 20 is then made. The interocclusal or freeway space is rechecked. With both trays 10, 20 in the mouth, the patient is again instructed to count from 1 to 10, repeating the number six a few times while counting in sequence. Approximately 1 mm of space between the wax trays 10, 20 should exist when the patient repeats the number six. If this is not present, enough wax should be removed from the upper and lower block members 18, 24 until the space is established.

The functional labial drape is checked. The proper position of the maxillary anterior teeth from a labial aspect is with the tips of the maxillary teeth at or palatal to the vermillion border of the lower lip, i.e., the wet-dry lip line. This is necessary for a patient to be able to assume a rest position. To check this, the patient speaks the "f" or "ph" sounds with the maxillary and mandibular trays 10, 20 in the mouth. The labial tip of the maxillary block 18 should be at the wet-dry lip line when the patient speaks those sounds.

The centric bite relation is then developed. Two divergent notches (not shown) are cut in the block 24 area of the mandibular tray 20 approximately 1 mm in depth in the first molar area. The tray 20 then is placed in the mouth. A sheet of yellow beeswax such as Mizzy Bite Rite Beeswax is heated and formed into a rectangular section having a width and depth of approximately ½ inch, and a length of 2 inches. After a section of softened beeswax is placed in each of the vacant bicuspid-molar areas of the maxillary tray 10 which is placed in the mouth, the patient is asked to open his mouth which is kept open for 30 seconds. Then while holding down the mandibular tray 20 with the index finger and thumb of each hand, the patient places his tongue on the back portion of the palate and closes his mouth at the same time. The wax is chilled and the patient opens his mouth. This procedure is repeated to make sure the mandible closes in the same recorded position.

Using a spatula the midline of the philtrum, the groove which connects the upper lip to the nose, is marked on the maxillary tray 10. While the patient smiles, the highest portion of the lip extension on tray 10 is marked. With lips at rest, the corner of the mouth on the maxillary tray 10 is also marked.

Master casts of the impressions in trays 10, 20 are next made by preparing suitable casting material. A cast mix is prepared of cast stone using one part water and four parts cast stone. This cast material is thoroughly mixed. One part cast plaster may be substituted for one part cast stone to speed the setting time. Silicone liquid (P.I.P.) surface tension reducer is sprayed on the impressions. This allows the impression to be separated easily from the cast. The cast mix is applied to each impression at one end thereof and is evenly distributed throughout by means of a vibrator. In this fashion, the air is displaced ahead of the cast mix which completely fills the impressions in the trays 10, 20. The cast mix filled impression is allowed to harden for approximately ½ hour.

Proper proportions of the master cast include a 16 mm thickness at the thinnest point, a mucobuccal fold area 3 mm deep, and a land area 5 mm wide.

The two casts are accurately sealed together so that they maintain the exact relationship of the original centric occlusal registration. The casts are mounted on an articulator either with a wet (plaster on the cast) or dry (prong) mounting so that the Camper's plane and the horizontal planes are parallel to the base of the articulator and the midline as marked on the blocks 18, 24 is in line with the midline of the articulator.

The artificial teeth can then be set. First the midline from the maxillary tray is transferred onto the maxillary cast and extended to the mandibular tray. The wax rim of the mandibular tray 20 should be flush anteriorally and buccally, i.e., near the cheek, posteriorally. The edge of this wax rim is the guide by which to set the maxillary teeth. The wax rim is then trimmed from the maxillary cast. The maxillary arch of fourteen teeth is positioned on the mandibular occlusal rim so that the occlusal portions rest on the mandibular occlusal rims with the occlusal facial tips of the teeth being flush with the facial aspect of the mandibular occlusal rim. The articulator is then closed so that the maxillary cast contacts the arch of fourteen teeth. The arch of fourteen teeth is set against the maxillary lower occlusal rim. The midlines should be checked so that they correspond. If there is sufficient space for the teeth, the teeth may be trimmed and/or the maxillary impression may have to be removed from the cast. The teeth are adhered to the cast by means of wax added thereto. If there is room, the impression acts as the base for the teeth. The maxillary teeth can be tried in the mouth for esthetics if desired. The mandibular wax occlusal rim is removed and mandibular teeth are set to articulate perfectly with the maxillary set. This is done by placing the occlusal surfaces of the mandibular tooth arch in proper position to the maxillary tooth arch and leuting the arches together with sticky wax. The articulator is then closed so that the mandibular tooth arch contacts the mandibular cast at the proper vertical dimension of rest and occlusion. If necessary, the arch of teeth may be separated to allow for better articulation. As before, these teeth are attached by means of wax added to the cast.

A final fitting is made after the maxillary and mandibular occlusal rims are placed in the mouth. The labial prominence is checked as well as the functional labial drape by having patient speak "f" and "ph" sounds. The tips of the maxillary anterior teeth should be checked so as not to extend beyond the "wet-dry" lip time. The freeway space is checked by having the patient count from one to ten. A 1 mm space between the maxillary and mandibular teeth should be maintained when the number six is repeated. The centric relation is checked by having the patient close his mouth while placing the tongue in the posterior palate area. The mandibular tray 20 should be held in position during this procedure. The centric relation registration is correct if the position of the teeth in the mouth is the same as on the articulator.

In maxillary denture construction, one of the most important factors is maintaining a stable and secure denture is the post palatal seal. It is a continuation of the peripheral seal in the posterior aspect of the denture. It is placed on the least movable aspect of the soft palate which is sufficiently displaceable to establish the seal. It extends across the palate from hamular notch to hamular notch. First the dentist locates the vibrating line by having the patient repeat the sound "ah" or "agh". This will demonstrate the most movable aspect of the soft palate as this area vibrates denoting the junction of the most movable and least movable aspect of the soft palate. The vibrating area is usually located slightly posterior to the fovea palatini and extends laterally to the hamular notch on each side. This is the posterior extension of the maxillary denture. The anterior border of the post palatal seal is established by locating the "blow line" or the line of flexture. This is accomplished by holding the patient's nostrils together with two fingers of one hand, pressing down the tongue with a tongue blade held in the other hand, and having the patient blow through the nose. This indicates the insertion of the soft tissues of the soft palate into the hard palate. This is compressible tissue area in which to create the posterior seal for the denture. These lines are transferred to the cast by means of indelible pencil applied to the tissue. The impression or wax trays 10, 20 on which the teeth are set is placed in the mouth. The line is then transferred to said trays 10, 20 and by means of said trays 10, 20 to the maxillary cast. The cast is then scraped to a depth which averages 1½ to 2 mm. The depth is dependent on the amount of tissue that can be displaced. The cast is scored by means of a Kingsley scraper and a cleoid-discoid instrument to its greatest depth posteriorally and is carried anteriorally in a gradual slope to the anterior border at 0°. This technique prevents the denture from being displaced when the patient functions.

Once trays 10, 20 have been completely adjusted and customized to the needs of a particular patient, they serve as models or replicas in the preparation of a final set of dentures by known conventional methods. The wax tray models 10, 20 once formed in their final form can be placed in a molding material. Upon melting or burning, the so-called burn-out procedure, the wax trays 10, 20 can be eliminated leaving behind a mold cavity which can then be used to cast or process a final restoration denture.

The molding material can be any conventional material such as plaster of paris, hydrocoloid or any other suitable molding material. Although such molds are useful for possibly only one or a few castings of a final product, the nature of the customized denture provided by this invention is such that no need exists for such mold beyond one suitable casting.

The final dentures can be made from a number of recently developed plastics such as acrylic, vinyl, styrene, and epoxy polymers. Of these, the acrylic plastics have been most widely used and accepted. Thus the final denture bases are preferably made of acrylic plastics.

The present invention also provides for the customizing of either an upper or lower denture form alone. If the patient needs an upper denture, the maxillary impression tray 10 is selected. Then those steps in the method of the present invention as described above and directed to customizing the upper denture form are followed. The lower dental arch is measured accordingly and an impression mold is made thereof. A model made from the impression mold can be used with the maxillary impression tray 10 on the articulator.

If the patient requires a lower denture, the mandibular impression tray 20 is selected and appropriate steps with respect thereto are followed. Similarly, the upper dental arch is measured and an impression made thereof to provide a model to be mounted with the mandibular impression tray 20 on the articulator.

The artificial teeth which are set on the maxillary and mandibular trays 10, 20 can be assembled either as individual units or as separate groups or blocks of integrally connected teeth as disclosed and illustrated in U.S. Pat. No. 3,644,996. Ths use of separate groups of teeth or teeth blocks are preferred since they provide for a quicker assembly. Moreover, the teeth blocks are more easily fabricated to conform to the shaped block members 18, 24. Similarly, the final dentures themselves are also preferably fabricated with the teeth blocks.

We claim:

1. An apparatus for making denture models used in fabricating dentures customized for a given patient, said apparatus being a moldable impression member adapted to conform to a portion of the mouth of said patient and to receive an impression of said portion, said impression member comprising an alterable block member representative of teeth and generally corresponding to the dimensions and positioning of said teeth, such that said apparatus upon being placed in the mouth of a patient and suitably formed and fitted thereto can be customized to provide a denture model, whereby the alterable block member is modified in accordance with customized measurements for determining the proper natural registration of the upper teeth relative to the lower teeth.

2. An apparatus for making upper denture models used in fabricating upper dentures customized for a given patient, said apparatus being a moldable impression member adapted to conform to an upper portion of the mouth of said patient and to receive an impression of said upper portion, said impression member comprising:
   an inner wall;
   an outer wall attached to the inner wall so as to define a channel disposed between said walls and adapted to receive and contact the alveolar ridge of the upper mouth;
   a base contiguous with the edges of the inner wall, said base adapted for contacting the palate of the upper mouth and retaining the impression thereof; and
   an alterable block member disposed on the nonimpression surface of said impression member and extending substantially along the length thereof, said block member being representative of teeth and generally corresponding to the dimensions and positioning of said teeth, such that said apparatus upon being placed in the lower portion of the mouth of a patient and suitably formed and fitted thereto is customized to provide a lower denture model, whereby the alterable block member is modified in accordance with customized measurements for determining the proper natural registration of the upper teeth relative to the lower teeth.

3. The apparatus of claim 2 wherein said impression member is arch shaped along the periphery of the outer wall.

4. The apparatus of claim 3 wherein said block member extends along a portion of the nonimpression surface of said impression member such that the bicuspid-molar regions are vacant.

5. An apparatus for making lower denture models used in fabricating lower dentures customized for a given patient, said apparatus being a moldable impression member adapted to conform to a lower portion of the mouth of said patient and to receive an impression of said lower portion, said impression member comprising:
   an inner wall;
   an outer wall attached to the inner wall so as to define a channel disposed between said walls and adapted to receive and contact the alveolar ridge of the lower mouth; and
   an alterable block member disposed on the nonimpression surface of said impression member and extending substantially along the length thereof, said block member being representative of teeth and generally corresponding to the dimensions and positioning of said teeth, such that said apparatus upon being placed in the lower portion of the mouth of a patient and suitably formed and fitted thereto is customized to provide a lower denture model, whereby the alterable block member is modified in accordance with customized measurements for determining the proper natural registration of the upper teeth relative to the lower teeth.

6. The article of claim 3 wherein said impression member is arch shaped along the periphery of the outer wall.

7. The article of claims 1, 4, or 6 wherein said impression member is made from a wax such as Mizzy Beeswax.

8. A method of making denture models for use in fabricating dentures customized for a given patient, comprising the steps of:
   a. selecting a maxillary and a mandibular moldable impression member, said maxillary and mandibular impression members being adapted to conform respectively to the upper and the lower portions of the mouth of said patient and to receive an impression of said respective portions, said impression members each comprising an alterable block member disposed on the non-impression surface of said impression member, said block member being representative of teeth and generally corresponding to the dimensions and positioning of said teeth, whereby the alterable block member is modified in accordance with customized measurements for determining the proper natural registration of the upper teeth relative to the lower teeth;
   b. making a first set of measurements of said patient and transferring said first set of measurements to said impression members, said first set of measurements including at least measuring the alveolar ridge heights from the corresponding mucobuccal folds;

c. making a first adjustment of said impression members in accordance with said first set of measurements;

d. placing said impression members in contact with their respective portions of the mouth of said patient and molding said impression members to receive the impressions and shape of said respective mouth portions;

e. making a second adjustment of said impression members, said second adjustment including at least developing the esthetic labial drape;

f. coating the impression surfaces of said impression members with an impressionable material and placing said impression members in contact with their respective portions of the mouth of said patient such that the impressionable material receives and retains the respective impressions thereof;

g. making a third adjustment of said impression members, said third adjustment including at least checking the functional labial drape;

h. making casts of the impression surfaces of said impression members and mounting said casts with said impression members being attached thereto in an articulator;

i. removing said block members and setting corresponding teeth in place thereof;

j. making a final fitting of said impression members in said patient's mouth, said final fitting including at least placing said impression members with teeth in place into the respective portions of the mouth; and k. establishing a post palatal seal for said maxillary impression member.

9. The method of claim 8 wherein making the first set of measurements of said patient further comprises:
measuring the areas of the midline, canine, and second molars; and wherein transferring said first set of measurements to said impression members comprises:
marking said alveolar ridge heights and said areas to said corresponding impression members by suitable markings thereon.

10. The method of claim 9 wherein the first adjustment comprises shaping said impression members to conform to the alveolar ridge heights.

11. The method of claim 8 wherein the second adjustment further comprises developing the horizontal plane of the lower edge of the maxillary block member.

12. The method of claim 11 further comprising developing the vertical dimension of rest.

13. The method of claim 13 further comprising establishing an interocclusal space of approximately 3 mms.

14. The method of claim 14 further comprising:
a. placing a mark on the nose and on the chin;
b. measuring a first length between said marks when said maxillary impression member is placed within the patient's mouth and the lips are just touching;
c. placing the mandibular impression member within the patient's mouth;
d. having the patient close the mouth so that said maxillary and mandibular block members are just touching;
e. reducing said mandibular block member such that it is substantially flush vertically and horizontally with said maxillary block member;
f. measuring a second length between said marks; and g. shaping said mandibular block member such that said second length is approximately 3 mms less than said first length.

15. The method of claim 14 further comprising:
a. providing a mandibular block member height such that the retromolar pad is generally bisected by said mandibular impression member's level plane;
b. evaluating the length approximately from the base of the nose to the end of the maxillary lip, thereby determining whether the patient has generally an average, a long, or a short said length;
c. having the patient maintain the lips slightly parted; and
d. shaping the lower edge of said maxillary block member such that approximately 2 mm extends below the lower edge of said maxillary lip when the patient has generally an average said length;
e. shaping the lower edge of said maxillary block member approximately level with the lower edge of said maxillary lip when the patient has generally a long said length; and
f. shaping the lower edge of said maxillary block member such that approximately 2 mm extends below the lower edge of said maxillary lip when the patient has generally a short said length.

16. The method of claim 14 or 15 comprising establishing approximately a 1 mm interocclusal space when the patient repeats the number six.

17. The method of claim 8 wherein the third adjustment of said impression members further comprises rechecking the interocclusal space so that said space is approximately at least 1 mm.

18. The method of claim 17 further comprising developing the centric occlusal registration.

19. The method of claim 18 further comprising marking the midline, cuspid, and high lip lines.

20. The method of claim 8 wherein the final fitting of said impression members comprises checking that the esthetic labial drape aspect, the functional labial drape, the interocclusal space, and the centric occlusal registration are maintained.

21. A method of making an upper denture model for use in fabricating an upper denture customized for a given patient, comprising the steps of:
a. selecting a maxillary moldable impression member, said maxillary impression member being adapted to conform to the upper portion of the mouth of said patient and to receive an impression of said upper portion, said impression member comprising an alterable block member disposed on the nonimpression surface of said impression member, said block member being representative of teeth and generally corresponding to the dimensions and positioning of said teeth, whereby the alterable block member is modified in accordance with customized measurements for determining the prior initial registration of the upper teeth relative to the lower teeth;
b. making a first set of measurements of said patient and transferring said first set of measurements to said impression member, said first set of measurements including at least measuring the alveolar ridge heights from the corresponding mucobuccal folds;
c. making a first adjustment of said first impression in accordance with said first set of measurements;
d. placing said impression member in contact with said upper portion of the mouth of said patient and molding said impression member to receive the impression and shape of said upper mouth portion;

e. making a second adjustment of said impression member, said second adjustment including at least developing the esthetic labial drape;

f. coating the impression surface of said impression member with an impressionable material and placing said impression member in contact with said upper portion of the mouth of said patient such that the impressionable material receives and retains the respective impression thereof;

g. making a third adjustment of said impression member, said third adjustment including at least checking the functional labial drape;

h. making a cast of the impression surface of said impression member and mounting said cast with said impression member being attached thereto in an articulator;

i. removing said block member and setting corresponding teeth in place thereof;

j. making a final fitting of said impression member in said patient's mouth, said final fitting including at least placing said impression member with teeth in place into the respective portion of the mouth; and k. establishing a post palatal seal.

22. A method of making a lower denture model for use in fabricating a lower denture customized for a given patient, comprising the steps of:

a. selecting a mandibular moldable impression member, said mandibular impression member being adapted to conform to the lower portion of the mouth of said patient and to receive an impression of said lower portion, said impression member comprising an alterable block member disposed on the nonimpression surface of said impression member, said block member being representative of teeth and generally corresponding to the dimensions and positioning of said teeth, whereby the alterable block member is modified in accordance with customized measurements for determining the proper natural registration of the upper teeth relative to the lower teeth;

b. making a first set of measurements of said patient and transferring said first set of measurements to said impression member, said first set of measurements including at least measuring the alveolar ridge heights from the corresponding mucobuccal folds;

c. making a first adjustment of said impression member in accordance with said first set of measurements;

d. placing said impression member in contact with said lower portion of the mouth of said patient and molding said impression member to receive the impression and shape of said lower mouth portion;

e. making a second adjustment of said impression member, said second adjustment including at least developing the esthetic labial drape;

f. coating the impression surface of said impression member with an impressionable material and placing said impression member in contact with said lower portion of the mouth of said patient such that the impressionable material receives and retains the respective impression thereof;

g. making a third adjustment of said impression member, said third adjustment including at least checking the functional labial drape;

h. making a cast of the impression surface of said impression member and mounting said cast with said impression member being attached thereto in an articulator;

i. removing said block member and setting corresponding teeth in place thereof; and j. making a final fitting of said impression members in said patient's mouth, said final fitting including at least placing said impression member with teeth in place into the respective portion of the mouth.

23. A method of making denture models for use in fabricating dentures customized for a given patient comprising the steps of:

a. selecting a maxillary and a mandibular moldable arch shaped wax impression member, said maxillary and mandibular wax impression members being adapted to conform respectively to the upper and lower portions of the mouth of said patient and to receive an impression of said respective portions, said wax impression members each comprising:

an inner wall;

an outer wall attached to the inner wall so as to define a channel disposed between said walls and adapted to receive and contact the alveolar ridge of the upper mouth; and an alterable block member disposed on the nonimpression surface of said impression member and extending substantially along the length thereof, said block member being representative of teeth and generally corresponding to the dimensions and positioning of said teeth;

said maxillary wax impression member further comprising a base contiguous with the edges of the inner wall, said base adapted for contacting the palate of the upper mouth and retaining the impression thereof, said maxillary block member being modified so that the bicuspid-molar regions are vacant, whereby the alterable block member is modified in accordance with customized measurements for determining the proper natural registration of the upper teeth relative to the lower teeth;

b. making a first set of measurements of said patient and transferring said first set of measurements to said wax impression members, said first set of measurements including at least measuring the alveolar ridge heights from the corresponding mucobuccal folds;

c. making a first adjustment of said wax impression members in accordance with said first set of measurements;

d. softening said wax impression members;

e. placing said wax impression members in contact with their respective portions of the mouth of said patient and molding said wax impression members to receive the impressions and shape of said respective mouth portions;

f. making a second adjustment of said wax impression members, said second adjustment including at least developing the esthetic labial drape;

g. coating the impression surfaces of said wax impression members with an impressionable material and placing said impression members in contact with their respective portions of the mouth of said patient such that the impressionable material receives and retains the respective impressions thereof;

h. making a third adjustment of said wax impression members, said third adjustment including at least checking the functional labial drape;

i. making casts of the impression surfaces of said wax impression members and mounting said casts with said impression members being attached thereto in an articulator so that the centric occlusal registration is maintained;

j. removing said block members and setting corresponding teeth in place thereof;

k. making a final fitting of said wax impression members in said patient's mouth, said final fitting including at least placing said wax impression members with teeth in place into the respective portions of the mouth; and l. establishing a post palatal seal for said maxillary wax impression member.

24. The method of claim 23 wherein making the first set of measurements of said patient further comprises:
    measuring the areas of the midline, canine, and second molars; and wherein transferring said first set of measurements to said impression members comprises:
    marking said alveolar ridge heights and said areas to said corresponding was impression members by suitable markings thereon.

25. The method of claim 23 wherein the first adjustment comprises shaping said wax impression members to conform to the alveolar ridge heights.

26. The method of claim 23 wherein the step of softening said wax impression members comprises placing said wax impression members in a water bath having a temperature approximately 120° F.

27. The method of claim 25 wherein developing the esthetic labial drape comprises suitably reducing the labial portion of the outer wall of said maxillary wax impression member such that the maxillary lip is esthetic in appearance.

28. The method of claim 23 wherein the second adjustment further comprises developing the horizontal plane of the lower edge of said maxillary block member.

29. The method of claim 28 wherein developing the horizontal plane comprises:
    a. evaluating the length approximately from the base of the nose to the end of the maxillary lip, thereby determining whether the patient has generally an average, a long, or a short said length;
    b. having the patient maintain the lips slightly parted; and
    c. shaping the lower edge of said maxillary block member such that approximately 1 mm extends below the lower edge of said maxillary lip when the patient has generally an average said length;
    d. shaping the lower edge of said maxillary block member approximately level with the lower edge of said maxillary lip when the patient has a generally long said length; and
    e. shaping the lower edge of said maxillary block member approximately level with the lower edge of said maxillary lip when the patient has generally a long said length; and
    f. shaping the lower edge of said maxillary block member such that approximately 2 mm extends below the lower edge of said maxillary lip when the patient has generally a short said length.

30. The method of claim 29 further comprising paralleling the lower edge of said maxillary block member to the interpapillary line.

31. The method of claim 25 further comprising developing the vertical dimension of rest.

32. The method of claim 31 further comprising establishing an interocclusal space of approximately 3 mms.

33. The method of claim 32 further comprising:
    a. placing a mark on the nose and on the chin;
    b. measuring a first length between said marks when said maxillary wax impression member is placed within the patient's mouth and the lips are just touching;
    c. placing said mandibular wax impression member within the patient's mouth;
    d. having the patient close the mouth so that said maxillary and mandibular block members are just touching;
    e. reducing said mandibular block member such that it is substantially flush vertically and horizontally with said maxillary block member;
    f. measuring a second length between said marks; and
    g. shaping said mandibular block member such that said second length is approximately 3 mms less than said first length.

34. The method of claim 32 further comprising:
    a. providing a mandibular block member height such that the retromolar pad is generally bisected by said mandibular wax impression member's level plane;
    b. evaluating the length approximately from the base of the nose to the end of the maxillary lip, thereby determining whether the patient has generally an average, a long, or a short said length;
    c. having the patient maintain the lips slightly parted; and
    d. shaping the lower edge of said maxillary block member such that approximately 1 mm extends below the lower edge of said maxillary lip when the patient has generally an average said length.
    e. shaping the lower edge of said maxillary block member approximately level with the lower edge of said maxillary lip when the patient has generally a long said length; and
    f. shaping the lower edge of said maxillary block member such that approximately 2 mm extends below the lower edge of said maxillary lip when the patient has generally a short said length.

35. The method of claim 33 or 34 comprising establishing approximately a 1 mm interocclusal space when the patient repeats the number six.

36. The method of claim 35 further comprising reducing said mandibular block member 1 mm at a time until a 1 mm interocclusal space is maintained when the patient repeats the number six.

37. The method of claim 23 wherein the third adjustment of said wax impression members further comprises rechecking the interocclusal space so that said space is approximately 3 mm.

38. The method of claim 37 further comprising sutiably reducing the maxillary and mandibular block members so that a 1 mm interocclusal space is maintained when the patient repeats the number six.

39. The method of claim 37 further comprising establishing that the edge of the maxillary block member is adjacent the vermillion borader of the lower lip during the rest position.

40. The method of claim 39 further comprising having the patient pronounce the f or ph sounds during which the edge of said maxillary block member is to be adjacent the vermillian border of the lower lip.

41. The method of claim 37 further comprising developing the centric occlusal registration.

42. The method of claim 41 further comprising placing softened wax int the vacant bicuspid-molar region of said maxillary wax impression member to develop a centric occlusal registration.

43. The method of claim 37 further comprising marking the midline, cuspid, and high lip lines on said maxillary wax impression member.

44. The method of claim 43 further comprising marking the philtrum midline on the maxillary tray.

45. The method of claim 44 further comprising marking the lip lines on said maxillary wax impression member when the lips are respectively at a smile position and at a rest position.

46. The method of claim 23 wherein the final fitting of said impression members comprises checking that the esthetic labial drape aspect, the functional labial drape, the interocclusal space, and the centric occlusal registration are maintained.

47. The method of claim 46 further comprising establishing a post palatal seal for said maxillary wax impression member.

* * * * *

UNITED STATES PATENT AND TRADEMARK OFFICE
CERTIFICATE OF CORRECTION

PATENT NO. : 4,245,988
DATED : January 20, 1981
INVENTOR(S) : William Cinotti, Harold Gelb, and Arthur Grieder It is certified that error appears in the above—identified patent and that said Letters Patent is hereby corrected as shown below:

In Column 8, line 17, "is maintaining" should be -- in maintaining --.

In Column 11, line 53, "claim 13" should be -- claim 12 --.

In Column 11, line 55, "claim 14" should be -- claim 13 --.

In Column 15, line 39, "claim 23" should be -- claim 25 --.

In Column 16, line 57, "sutiably" should be -- suitably --.

In Column 16, line 63, "borader" should be -- border --.

In Column 17, line 4, "int" should be -- into --.

Signed and Sealed this

Ninth Day of June 1981

[SEAL]

Attest:

RENE D. TEGTMEYER

Attesting Officer    Acting Commissioner of Patents and Trademarks